(12) United States Patent
Tang et al.

(10) Patent No.: US 10,330,650 B2
(45) Date of Patent: Jun. 25, 2019

(54) HIGH PERFORMANCE LIQUID CHROMATOGRAPHY METHOD FOR POLYPEPTIDE MIXTURES

(71) Applicant: HYBIO PHARMACEUTICAL CO., LTD., Shenzhen (CN)

(72) Inventors: Yangming Tang, Shenzhen (CN); Gang He, Shenzhen (CN); Guotao Li, Shenzhen (CN); Anjin Tao, Shenzhen (CN); Jiancheng Yuan, Shenzhen (CN)

(73) Assignee: HYBIO PHARMACEUTICAL CO., LTD., Shenzhen (CN)

( * ) Notice: Subject to any disclaimer, the term of this patent is extended or adjusted under 35 U.S.C. 154(b) by 137 days.

(21) Appl. No.: 15/559,428

(22) PCT Filed: Apr. 28, 2015

(86) PCT No.: PCT/CN2015/077690
§ 371 (c)(1),
(2) Date: Sep. 19, 2017

(87) PCT Pub. No.: WO2016/172855
PCT Pub. Date: Nov. 3, 2016

(65) Prior Publication Data
US 2018/0080909 A1    Mar. 22, 2018

(51) Int. Cl.
  *G01N 1/18*    (2006.01)
  *G01N 33/00*   (2006.01)
  (Continued)

(52) U.S. Cl.
  CPC ............. *G01N 30/34* (2013.01); *A61K 38/03* (2013.01); *B01D 15/325* (2013.01);
  (Continued)

(58) Field of Classification Search
  CPC .......... G01N 1/18; G01N 33/00; G01N 30/34; G01N 21/33; G01N 30/74; A61K 38/03
  (Continued)

(56) References Cited

U.S. PATENT DOCUMENTS

2002/0010319 A1* 1/2002 Ansaldi ............... C07K 1/18
  530/387.1
2005/0202483 A1* 9/2005 Sanderson ........... C12Q 1/6883
  435/6.11

(Continued)

FOREIGN PATENT DOCUMENTS

CN    103335873 A    10/2013
WO    2012123959 A2   9/2012

*Primary Examiner* — Brian J. Sines
(74) *Attorney, Agent, or Firm* — Gokalp Bayramoglu

(57) ABSTRACT

The present invention relates to a high performance liquid chromatography method for polypeptide mixtures. Specifically, the method including the following steps: step (1): preparing a solution of the glatiramer acetate to be tested; step (2): performing gradient elution on a sample to be tested with an anion exchange liquid chromatography, a cation exchange liquid chromatography, or a reversed-phase liquid chromatography; step (3): determining a peak area corresponding to each component of the glatiramer acetate, comparing the peak area with to a peak area of a reference substance to determine whether the content of each component of the sample to be tested is in a qualified range.

15 Claims, 7 Drawing Sheets

(51) Int. Cl.
- G01N 30/34 (2006.01)
- G01N 21/33 (2006.01)
- G01N 30/74 (2006.01)
- A61K 38/03 (2006.01)
- C07K 14/00 (2006.01)
- B01D 15/32 (2006.01)
- B01D 15/36 (2006.01)
- G01N 30/86 (2006.01)
- G01N 30/88 (2006.01)
- G01N 33/68 (2006.01)
- C07K 1/18 (2006.01)
- C07K 1/20 (2006.01)

(52) U.S. Cl.
CPC ......... *B01D 15/362* (2013.01); *B01D 15/363* (2013.01); *C07K 14/00* (2013.01); *G01N 21/33* (2013.01); *G01N 30/74* (2013.01); *G01N 30/8631* (2013.01); *G01N 30/88* (2013.01); *G01N 33/6803* (2013.01); *C07K 1/18* (2013.01); *C07K 1/20* (2013.01); *G01N 2030/8831* (2013.01)

(58) Field of Classification Search
USPC .................................. 436/86, 174, 177, 178
See application file for complete search history.

(56) References Cited

U.S. PATENT DOCUMENTS

| | | |
|---|---|---|
| 2009/0263347 A1 | 10/2009 | Jiang et al. |
| 2009/0264630 A1* | 10/2009 | Eriksson ............ B01D 15/3804 530/413 |
| 2012/0123089 A1* | 5/2012 | Dave .................... B01D 15/166 530/305 |
| 2014/0030275 A1* | 1/2014 | Park ...................... C07K 16/18 424/172.1 |
| 2015/0037359 A1* | 2/2015 | Schellenberger .... C07K 5/0205 424/178.1 |

* cited by examiner

HIGH PERFORMANCE LIQUID CHROMATOGRAPHY METHOD FOR POLYPEPTIDE MIXTURES

CROSS REFERENCE TO RELATED APPLICATIONS

This application is the national phase entry of International Application No. PCT/CN2015/077690, filed on Apr. 28, 2015, the entire contents of which are incorporated herein by reference.

TECHNICAL FIELD

The present invention relates to the field of biological medicines, especially to a high performance liquid chromatography method for polypeptide mixtures.

BACKGROUND OF THE INVENTION

Glatiramer acetate (GA) is a synthetic peptide mixture (relative molecular weight: 4700-11000 Daltons), a random polymer consisting of four kinds of amino acids: L-alanine, L-glutamic, L-tyrosine and L-lysine, with a length of 45-100 amino acids. The molar ratios of each kind of amino acids are approximately 0.392-0.462, 0.129-0.153, 0.086-0.100 and 0.300-0.374. This drug is manufactured by the Israeli TEVA pharmaceutical factory (TEVA) with a trade name of Copaxone®. It was approved for the treatment of multiple sclerosis by FDA in 1996, and there are two kinds of products, water needle and freeze-dried powder needle, both of which are administered by subcutaneous injection.

Glatiramer acetate is a copolymer with high continuity, the structure of the glatiramer acetate is as follows:

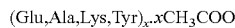

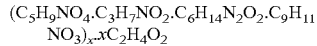    CAS-147245-92-9

For the manufacturers imitating the drug, the compositional differences between the imitation of glatiramer acetate and the control group of the glatiramer acetate can only be examined based on some of the inherent properties of the drug.

The difference between a sample and a commercial product (reference substance) is examined by gradient elution in an anion exchange liquid chromatography, a cation liquid chromatography and/or a reversed-phase liquid chromatography in the present invention based on the electric charge, polar or nonpolar character of the sample in different buffer solutions.

As the glatiramer acetate is a copolymer with high continuity, it is difficult to clarify the various components with only one separation method. A size exclusion method is used in the prior art for a simple separation and analysis (dividing a single peak into several components, and then collecting and analyzing the components). Thus, the prior art is very tedious. It is very necessary to develop an analytical method for an effective separation of the components of the glatiramer acetate.

SUMMARY OF THE INVENTION

The present invention relates to a method performing linear or stepped gradient elution on a glatiramer acetate with a high-performance liquid chromatography and determining whether the content of each component of the glatiramer acetate is qualified.

The method comprising the following steps:
step (1): preparing a solution of the glatiramer acetate to be tested;
step (2): performing gradient elution on a sample to be tested with an anion exchange liquid chromatography, a cation exchange liquid chromatography, or a reversed-phase liquid chromatography;
step (3): determining a peak area corresponding to each component of the glatiramer acetate, comparing the peak area with to a peak area of a reference substance to determine whether the content of each component of the sample to be tested is in a qualified range.

The elution gradient in step (2) is as follow.

The chromatographic conditions used in the anion exchange liquid chromatography in step (2) are as follows.

carboxyl-bonded polystyrene-divinylbenzene particle with a particle diameter of 1.7-10 μm is used as a packing material for a chromatographic column;

a solution containing 10-50 mM tris(hydroxymethyl)aminomethane hydrochloride is used as mobile phase A, wherein pH of the mobile phase A is adjusted to 10-12 with a NaOH solution;

a solution containing 10-50 mM tris(hydroxymethyl)aminomethane hydrochloride and 0.5-1.5 M NaCl is used as mobile phase B, wherein pH of the mobile phase B is adjusted to 8-10 with a hydrochloric acid solution;

injection volume is 5-50 uL, the concentration of the sample is 1-20 mg/mL;

a flow rate is 0.5-1.5 mL/min, the time for the gradient elution is 50-250 min;

different forms of elution gradients are used in gradient elution;

column temperature is 25-50° C.;

the elution gradient is as follow:

a total time of the gradient elution is divided into N steps uniformly for gradient elution sequentially, wherein $2 \leq N \leq 20$; in the first N−1 steps, the proportion of the mobile phase A is gradually reduced from 100% to 50%, and the proportion of the mobile phase B is gradually increased from 0 to 50%; in the N-th step, the proportion of the mobile phase A is 100%, and the proportion of the mobile phase B is 0;

preferably, $5 \leq N \leq 15$, more preferably, $8 \leq N \leq 12$, most preferably, N=10.

The chromatographic conditions used in the cation exchange liquid chromatography in step (2) are as follows:

tertiary ammonium-bonded polystyrene-divinylbenzene particle with a particle diameter of 1.7-10 μm is used as a packing material for a chromatographic column;

a solution containing 10-50 mM 2-(N-morpholino) ethanesulfonic acid and 0.5-5 mM EDTA is used as mobile phase A, wherein pH of the mobile phase A is adjusted to 4-6 with a NaOH solution;

a solution containing 10-50 mM 2-(N-morpholino) ethanesulfonic acid, 0.5-5 mM EDTA, and 1-2.5 M NaCl is used as mobile phase B, wherein pH of the mobile phase B is adjusted to 5-7 with a hydrochloric acid solution;

injection volume is 5-50 uL, the concentration of the sample is 1-20 mg/mL;

a flow rate is 0.5-1.5 mL/min, the time for the gradient elution is 50-250 min;

the elution gradient is that different forms of elution gradients are used in gradient elution;

column temperature is 25-50° C.;

the elution gradient is as follows:

a total time of the gradient elution is divided into N steps uniformly for gradient elution sequentially, wherein 2≤N≤20; in the first N−1 steps, the proportion of the mobile phase A is gradually reduced from 100% to 0%, and the proportion of the mobile phase B is gradually increased from 0 to 100%; in the N-th step, the proportion of the mobile phase A is 90%, and the proportion of the mobile phase B is 10%;

preferably, 5≤N≤15, more preferably, 8≤N≤12, most preferably, N=10.

The chromatographic conditions used in the reversed-phase liquid chromatography in step (2) are as follows:

C18-bonded, C12-bonded, C8-bonded, or C4-bonded silica particle with a particle diameter of 1.7-10 μm is used as a packing material for a chromatographic column;

acetonitrile is used as mobile phase A;

a solution containing 30-80 mM ammonium sulfate is used as mobile phase B, wherein pH of the mobile phase B is adjusted to 2-3 with a phosphoric acid solution; or 0.1% trifluoroacetic solution is used as the mobile phase B;

injection volume is 5-50 uL, the concentration of the sample is 1-20 mg/mL;

a flow rate is 0.5-1.5 mL/min, the time for the gradient elution is 50-250 min;

the elution gradient is that different forms of elution gradients are used in gradient elution;

column temperature is 25-50° C.;

the gradient elution is as follows:

a total time of the gradient elution is divided into N steps uniformly for gradient elution sequentially, wherein 2≤N≤20; in the first N−1 steps, the proportion of the mobile phase A is gradually increased from 5% to 40%, and the proportion of the mobile phase B is gradually reduced from 95% to 60%; in the N-th step, the proportion of the mobile phase A is 90%, and the proportion of the mobile phase B is 10%;

preferably, 5≤N≤15, more preferably, 8≤N≤12, most preferably, N=10.

The detection analysis in step (3) uses an ultraviolet detector to detect a wavelength of 260-280 nm.

When the fluorescence detector is used, its excitation wavelength is 230 nm and its emission wavelength is 300 nm.

BRIEF DESCRIPTION OF THE DRAWINGS

FIG. 1-2 is a chromatographic analysis diagram of a test sample in embodiment 2.

FIG. 1-3 is a chromatographic analysis diagram of a test sample in embodiment 3.

FIG. 1-4 is a chromatographic analysis diagram of a test sample in embodiment 4.

FIG. 1-5 is a chromatographic analysis diagram of a test sample in embodiment 5.

FIG. 2-1 is a chromatographic analysis diagram of a test sample in embodiment 7.

FIG. 2-2 is a chromatographic analysis diagram of a test sample in embodiment 8.

FIG. 2-3 is a chromatographic analysis diagram of a test sample in embodiment 9.

FIG. 2-4 is a chromatographic analysis diagram of a test sample in embodiment 10.

FIG. 3-1 is a chromatographic analysis diagram of a test sample in embodiment 12.

FIG. 3-2 is a chromatographic analysis diagram of a test sample in embodiment 13.

FIG. 3-3 is a chromatographic analysis diagram of a test sample in embodiment 14.

FIG. 3-4 is a chromatographic analysis diagram of a test sample in embodiment 15.

FIG. 3-5 is a chromatographic analysis diagram of a test sample in embodiment 16.

DETAILED DESCRIPTION OF THE INVENTION

Embodiment 1

Figure 1:
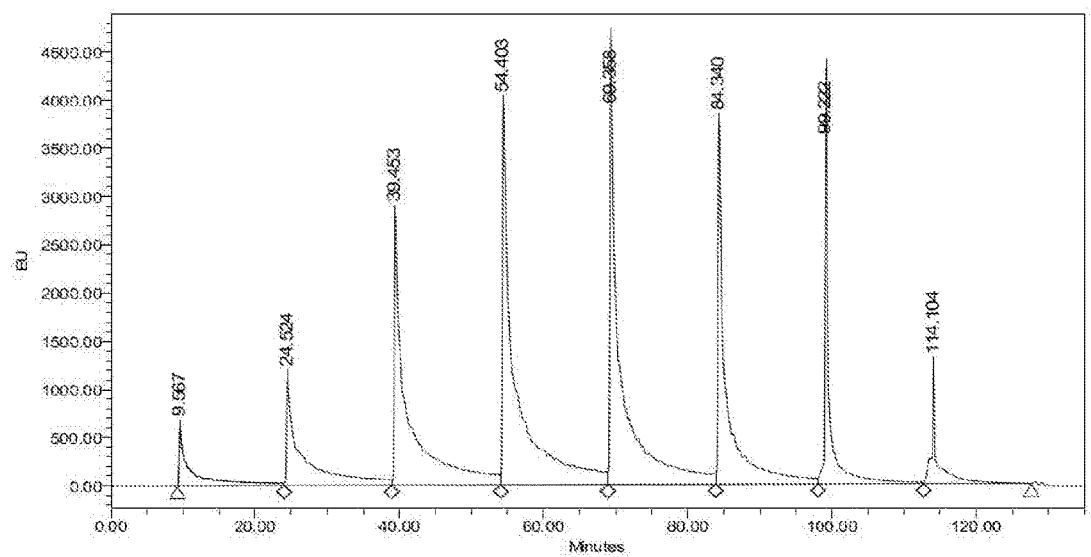
FIG. 1-1 is a chromatographic analysis diagram of a test sample in embodiment 1.

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 150 mm and a diameter of 4.6 mm. The packing material for the chromatographic column is polystyrene-divinylbenzene particles with a particle diameter of 3 μm. The mobile phase A is 20 mM tris(hydroxymethyl)aminomethane hydrochloride, the pH of which is adjusted to 11.2 with a NaOH solution. The mobile phase B is 20 mM tris(hydroxymethyl)aminomethane hydrochloride containing 1 M NaCl, the pH of which is adjusted to 9.8 with a hydrochloric acid solution. The proportions of the mobile phase A and mobile phase B are set according to the following Table 1. Mobile phase solutions are added to dissolve commercial glatiramer acetate product (hereinafter referred to as "reference substance") and pre-production glatiramer acetate sample (hereinafter referred to as "test sample"), respectively, to obtain a solution with a glatiramer acetate concentration of 20 mg/mL for examination. The injection volume is 25 μL. The flow rate is 0.8 mL/min. The column temperature is 30° C. The proportions of each component are shown in Table 2. The chromatographic analysis diagram of a test sample is shown in FIG. 1-1.

TABLE 1

Proportions of mobile phase A and mobile phase B in embodiment 1

| Time (min) | Mobile phase A (%) | Mobile phase B (%) |
|---|---|---|
| 0 | 100 | 0 |
| 15 | 100 | 0 |
| 15.1 | 97.5 | 2.5 |
| 30 | 97.5 | 2.5 |
| 30.1 | 95 | 5 |
| 45 | 95 | 5 |
| 45.1 | 90 | 10 |
| 60 | 90 | 10 |
| 60.1 | 87.5 | 12.5 |
| 75 | 87.5 | 12.5 |
| 75.1 | 85 | 15 |
| 90 | 85 | 15 |
| 90.1 | 80 | 20 |
| 105 | 80 | 20 |
| 105.1 | 70 | 30 |
| 120 | 70 | 30 |
| 120.1 | 50 | 50 |
| 135 | 50 | 50 |
| 135.1 | 100 | 0 |
| 140 | 100 | 0 |

TABLE 2

Comparisons and analyses of compositions of anion exchanges between three batches of reference substances and three batches of test samples

| Batch number | Component proportions of each elution peak (%) | | | | | | | |
|---|---|---|---|---|---|---|---|---|
| | 1 | 2 | 3 | 4 | 5 | 6 | 7 | 8 |
| Reference Substance 1 | 4.55 | 33.58 | 20.55 | 16.08 | 11.37 | 6.89 | 5.54 | 1.45 |
| Reference Substance 2 | 3.38 | 35.15 | 21.16 | 16.08 | 11.06 | 6.69 | 5.15 | 1.32 |
| Reference Substance 3 | 4.05 | 33.39 | 20.28 | 16.19 | 11.51 | 7.41 | 5.68 | 1.48 |
| Test sample 1 | 1.63 | 27.94 | 20.52 | 17.62 | 13.38 | 8.99 | 7.83 | 2.08 |
| Test sample 2 | 3.77 | 29.51 | 19.87 | 17.14 | 12.73 | 8.49 | 6.89 | 1.59 |
| Test sample 3 | 3.85 | 31.63 | 20.48 | 17.05 | 11.97 | 7.81 | 5.91 | 1.29 |

Embodiment 2

Figures 1, 2:
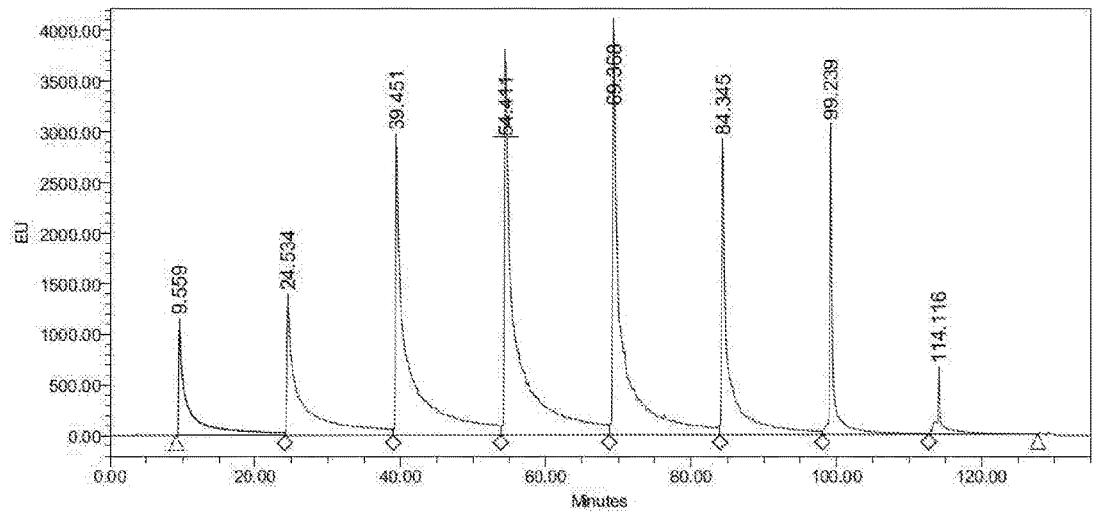

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 150 mm and a diameter of 4.6 mm. The packing material for the chromatographic column is polystyrene-divinylbenzene particles with a particle diameter of 5 μm. The mobile phase A is 10 mM tris(hydroxymethyl)aminomethane hydrochloride, the pH of which is adjusted to 10 with a NaOH solution. The mobile phase B is 10 mM tris(hydroxymethyl)aminomethane hydrochloride containing 1.5 M NaCl, the pH of which is adjusted to 8 with a hydrochloric acid solution. The proportions of the mobile phase A and mobile phase B are set according to the following Table 1. Mobile phase solutions are added to dissolve the reference substance or the test sample, respectively, to obtain a solution of 20 mg/mL for examination. The injection volume is 15 μL. The flow rate is 0.5 mL/min. The column temperature is 25° C. A chromatographic analysis diagram of a test sample is shown in FIG. 1-2.

Embodiment 3

Figures 1, 2, 3:
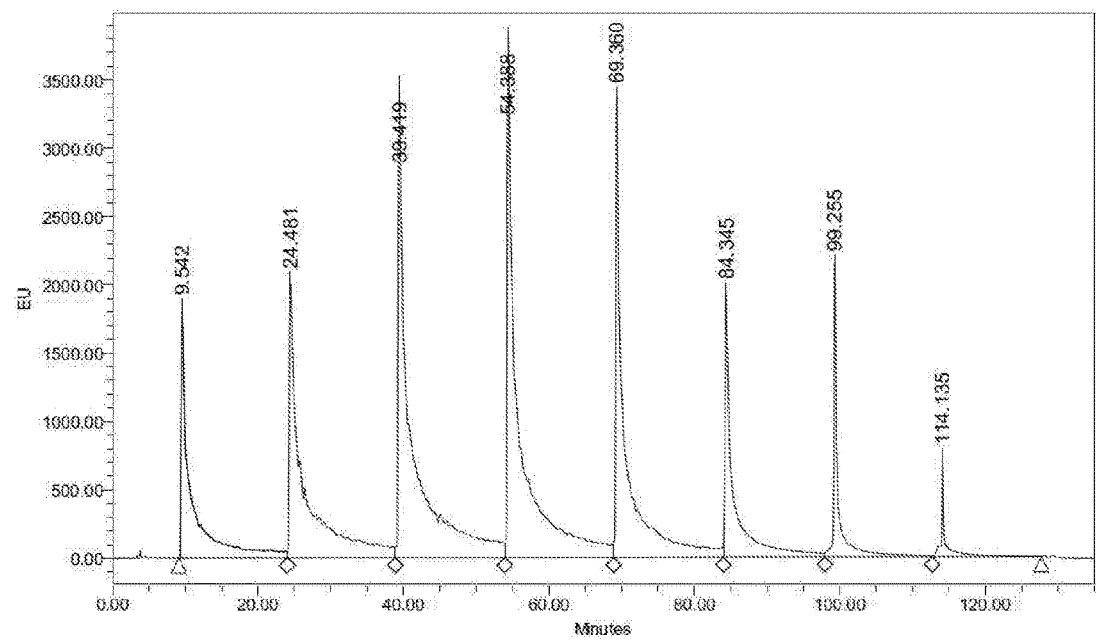

A Waters 2695 high performance liquid chromatography and a 2489 multiwavelength fluorescence detector are used. The wavelength is 275 nm. The chromatographic column has a length of 150 mm and a diameter of 4.6 mm. The packing material for the chromatographic column is polystyrene-divinylbenzene particles with a particle diameter of 10 μm. The mobile phase A is 50 mM tris(hydroxymethyl)aminomethane hydrochloride, the pH of which is adjusted to 12 with a NaOH solution. The mobile phase B is 50 mM tris(hydroxymethyl)aminomethane hydrochloride containing 0.5 M NaCl, the pH of which is adjusted to 10 with a hydrochloric acid solution. The proportions of the mobile phase A and mobile phase B are set according to the following Table 1. Mobile phase solutions are added to dissolve the reference substance or the test sample, respectively, to obtain a solution of 10 mg/mL for examination. The injection volume is 50 μL. The flow rate is 15 mL/min. The column temperature is 50° C. A chromatographic analysis diagram of a test sample is shown in FIG. 1-3.

Embodiment 4

A Waters 2695 high performance liquid chromatography and a 2489 multiwavelength fluorescence detector are used. The wavelength is 275 nm. The chromatographic column has a length of 150 mm and a diameter of 4.6 mm. The packing material for the chromatographic column is polystyrene-divinylbenzene particles with a particle diameter of 3 The mobile phase A is 30 mM tris(hydroxymethyl)aminomethane hydrochloride, the pH of which is adjusted to 10 with a NaOH solution. The mobile phase B is 30 mM tris(hydroxymethyl)aminomethane hydrochloride containing 1 M NaCl, the pH of which is adjusted to 8 with a hydrochloric acid solution. The proportions of the mobile phase A and mobile phase B are set according to the following Table 3. Mobile phase solutions are added to dissolve the reference substance or the test sample, respectively, to obtain a solution of 10 mg/mL for examination. The injection volume is 25 μL. The flow rate is 0.8 mL/min. The column temperature is 40° C. A chromatographic analysis diagram of a test sample is shown in FIG. 1-4.

TABLE 3

Proportions of mobile phase A and mobile phase B in embodiment 4

| Time (min) | Mobile phase A (%) | Mobile phase B (%) |
|---|---|---|
| 0 | 100 | 0 |
| 15 | 95 | 5 |
| 30 | 92.5 | 7.5 |
| 45 | 90 | 10 |
| 60 | 87.5 | 12.5 |
| 75 | 85 | 15 |
| 90 | 80 | 20 |
| 105 | 70 | 30 |
| 120 | 50 | 50 |
| 135 | 100 | 0 |
| 150 | 100 | 0 |

Embodiment 5

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 150 mm and a diameter of 4.6 mm. The packing material for the chromatographic column is polystyrene-divinylbenzene particles with a particle diameter of 3 The mobile phase A is 20 mM tris(hydroxymethyl)aminomethane hydrochloride, the pH of which is adjusted to 11.2 with a NaOH solution. The mobile phase B is 20 mM tris(hydroxymethyl)aminomethane hydrochloride containing 1 M NaCl, the pH of which is adjusted to 9.8 with a hydrochloric acid solution. The proportions of the mobile phase A and mobile phase B are set according to the following Table 4. Mobile phase solutions are added to dissolve the reference substance or the test sample, respectively, to obtain a solution of 20 mg/mL for examination. The injection volume is 25 μL. The flow rate is 1 mL/min. The column temperature is 30° C. A chromatographic analysis diagram of a test sample is shown in FIG. 1-5. It can be seen that the components of the samples cannot be effectively separated under the elution condition.

TABLE 4

Proportions of mobile phase A and mobile phase B in embodiment 5

| Time (min) | Mobile phase A (%) | Mobile phase B (%) |
|---|---|---|
| 0 | 100 | 0 |
| 10 | 100 | 0 |
| 30 | 0 | 100 |
| 40 | 0 | 100 |
| 41 | 100 | 0 |
| 55 | 100 | 0 |

Embodiment 6

A Waters 2695 high performance liquid chromatography and a 2498 multiwavelength fluorescence detector are used. The wavelength is 275 nm. The chromatographic column has a length of 150 mm and a diameter of 4.6 mm. The packing material for the chromatographic column is polystyrene-divinylbenzene particles with a particle diameter of 3 μm. The mobile phase A is 20 mM tris(hydroxymethyl)aminomethane hydrochloride, the pH of which is adjusted to 11.2 with a NaOH solution. The mobile phase B is 20 mM tris(hydroxymethyl)aminomethane hydrochloride containing 1 M NaCl, the pH of which is adjusted to 9.8 with a hydrochloric acid solution. The proportions of the mobile phase A and mobile phase B are set according to the following Table 6. Mobile phase solutions are added to dissolve the reference substance or the test sample, respectively, to obtain a solution of 20 mg/mL for examination.

The injection volume is 25 μL. The flow rate is 0.8 mL/min. The column temperature is 30° C. The proportions of each component are shown in Table 6.

TABLE 5

Proportions of mobile phase A and mobile phase B in embodiment 6

| Time (min) | Mobile phase A (%) | Mobile phase B (%) |
|---|---|---|
| 0 | 100 | 0 |
| 10 | 100 | 0 |
| 10.1 | 97 | 3 |
| 15 | 97 | 3 |
| 15.1 | 93 | 7 |
| 20 | 93 | 7 |
| 20.1 | 90 | 10 |
| 30 | 90 | 10 |
| 30.1 | 85 | 15 |
| 40 | 85 | 15 |
| 40.1 | 80 | 20 |
| 50 | 80 | 20 |
| 50.1 | 75 | 25 |
| 60 | 75 | 25 |
| 60.1 | 70 | 30 |
| 75 | 70 | 30 |
| 75.1 | 65 | 35 |
| 85 | 65 | 35 |
| 85.1 | 60 | 40 |
| 95 | 60 | 40 |
| 95.1 | 55 | 45 |
| 105 | 55 | 45 |
| 105.1 | 50 | 50 |
| 120 | 50 | 50 |
| 120.1 | 100 | 0 |
| 140 | 100 | 0 |

TABLE 6

Comparisons and analyses of compositions of anion exchanges between three batches of reference substances and three batches of test samples

| Batch number | 1 | 2 | 3 | 4 | 5 | 6 | 7 | 8 | 9 | 10 |
|---|---|---|---|---|---|---|---|---|---|---|
| Reference Substance 1 | 3.32 | 32.16 | 19.55 | 16.94 | 10.95 | 6.02 | 5.21 | 2.26 | 1.96 | 1.63 |
| Reference Substance 2 | 4.02 | 34.51 | 20.86 | 15.38 | 10.06 | 6.51 | 4.56 | 1.32 | 1.59 | 1.20 |
| Reference Substance 3 | 3.65 | 32.99 | 19.88 | 15.79 | 11.11 | 7.01 | 5.28 | 1.48 | 1.67 | 1.13 |
| Test sample 1 | 2.33 | 26.61 | 20.19 | 17.29 | 13.05 | 8.66 | 7.50 | 1.75 | 1.48 | 1.16 |
| Test sample 2 | 3.39 | 29.13 | 19.49 | 16.76 | 12.35 | 8.11 | 6.51 | 1.59 | 1.52 | 1.14 |
| Test sample 3 | 3.44 | 31.22 | 20.07 | 16.64 | 11.56 | 7.4 | 5.50 | 1.60 | 1.27 | 1.29 |

Cation Exchange Liquid Chromatography (Embodiments 7-10)

Embodiments 7

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 250 mm and a diameter of 4.6 mm. The packing material for the chromatographic column is tertiary ammonium-bonded polystyrene-divinylbenzene particles with a particle diameter of 5 μm. The mobile phase A is 20 mM 2-(N-morpholino) ethanesulfonic acid containing 1 mM EDTA, the pH of which is adjusted to 5.2 with a NaOH solution. The mobile phase B is 20 mM 2-(N-morpholino) ethanesulfonic acid containing 2 mM EDTA and 2 M NaCl, the pH of which is adjusted to 5.8 with a NaOH solution. The proportions of the mobile phase A and mobile phase B are set according to the following Table 7. Mobile phase solutions are added to dissolve the reference substance or the test sample, respectively, to obtain a solution of 20 mg/mL for examination. The injection volume is 25 µL. The flow rate is 1 mL/min. The column temperature is 30° C. A chromatographic analysis diagram of a test sample is shown in FIG. 2-1.

TABLE 7

Proportions of mobile phase A and mobile phase B in embodiment 7

| Time (min) | Mobile phase A (%) | Mobile phase B (%) |
| --- | --- | --- |
| 0 | 90 | 10 |
| 15 | 90 | 10 |
| 15.1 | 80 | 20 |
| 30 | 80 | 20 |
| 30.1 | 70 | 30 |
| 45 | 70 | 30 |
| 45.1 | 60 | 40 |
| 60 | 60 | 40 |
| 60.1 | 50 | 50 |
| 75 | 50 | 50 |
| 75.1 | 40 | 60 |
| 90 | 40 | 60 |
| 90.1 | 30 | 70 |
| 105 | 30 | 70 |
| 105.1 | 20 | 80 |
| 120 | 20 | 80 |
| 120.1 | 0 | 100 |
| 135 | 0 | 100 |
| 135.1 | 90 | 10 |
| 150 | 90 | 10 |

TABLE 8

Comparison and analyses of compositions of anion exchanges between three batches of reference substances and three batches of test samples

| Batch number | Component proportions of each elution peak (%) | | | | | | | | |
| --- | --- | --- | --- | --- | --- | --- | --- | --- | --- |
| | 1 | 2 | 3 | 4 | 5 | 6 | 7 | 8 | 9 |
| Reference Substance 1 | 7.55 | 10.55 | 13.24 | 14.98 | 15.00 | 13.02 | 10.16 | 7.42 | 8.08 |
| Reference Substance 2 | 6.73 | 10.57 | 13.40 | 15.11 | 15.06 | 13.02 | 9.98 | 7.44 | 8.70 |
| Reference Substance 3 | 7.36 | 10.13 | 12.64 | 14.42 | 14.67 | 13.06 | 10.26 | 7.89 | 9.57 |
| Test sample 1 | 5.84 | 8.13 | 11.18 | 13.69 | 14.72 | 13.68 | 11.24 | 9.08 | 12.44 |
| Test sample 2 | 6.80 | 9.38 | 12.16 | 14.20 | 14.76 | 13.25 | 10.47 | 8.06 | 10.93 |
| Test sample 3 | 7.06 | 9.40 | 12.38 | 14.54 | 14.96 | 13.15 | 10.26 | 7.83 | 1.44 |

Embodiments 8

A Waters 2695 high performance liquid chromatography and a 2489 multiwavelength fluorescence detector are used. The wavelength is 275 nm. The chromatographic column has a length of 250 mm and a diameter of 4.6 mm. The packing material for the chromatographic column is tertiary ammonium-bonded polystyrene-divinylbenzene particle with a particle diameter of 10 µm. The mobile phase A is 10 mM 2-(N-morpholino) ethanesulfonic acid containing 0.5 mM EDTA, the pH of which is adjusted to 4 with a NaOH solution. The mobile phase B is 10 mM 2-(N-morpholino) ethanesulfonic acid containing 5 mM EDTA and 2 M NaCl, the pH of which is adjusted to 7 with a NaOH solution. The proportions of the mobile phase A and mobile phase B are set according to the following Table 7. Mobile phase solutions are added to dissolve the reference substance or the test sample, respectively, to obtain a solution of 20 mg/mL for examination. The injection volume is 15 µL. The flow rate is 1 mL/min. The column temperature is 25° C. A chromatographic analysis diagram of a test sample is shown in FIG. 2-2.

Embodiments 9

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 250 mm and a diameter of 4.6 mm. The packing material for the chromatographic column is tertiary ammonium-bonded polystyrene-divinylbenzene particle with a particle diameter of 5 µm. The mobile phase A is 50 mM 2-(N-morpholino) ethanesulfonic acid containing 1 mM EDTA, the pH of which is adjusted to 5.2 with a NaOH solution. The mobile phase B is 20 mM 2-(N-morpholino) ethanesulfonic acid containing 2 mM EDTA and 2 M NaCl, the pH of which is adjusted to 5 with a NaOH solution. The proportions of the mobile phase A and mobile phase B are set according to the following Table 7. Mobile phase solutions are added to dissolve the reference substance or the test sample, respectively, to obtain a solution of 10 mg/mL for examination. The injection volume is 50 µL. The flow rate is 1 mL/min. The column temperature is 30° C. A chromatographic analysis diagram of a test sample is shown in FIG. 2-3.

Embodiments 10

Figures 1, 2, 3, 4:
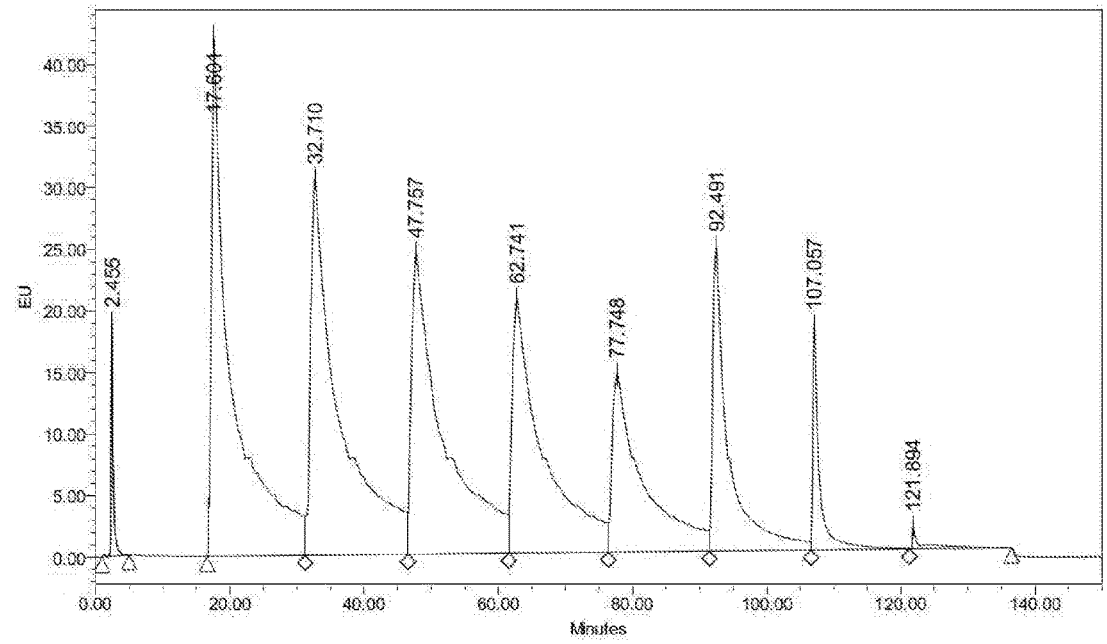

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 250 mm and a diameter of 4.6 mm. The packing material for the chromatographic column is tertiary ammonium-bonded polystyrene-divinylbenzene particle with a particle diameter of 5 µm. The mobile phase A is 20 mM 2-(N-morpholino) ethanesulfonic acid containing 1 mM EDTA, the pH of which is adjusted to 5.2 with a NaOH solution. The mobile phase B is 20 mM 2-(N-morpholino) ethanesulfonic acid containing 2 mM EDTA and 2 M NaCl, the pH of which is adjusted to 5.8 with a NaOH solution. The proportions of the mobile phase A and mobile phase B are set according to the following Table 9. Mobile phase solutions are added to dissolve the reference substance or the test sample, respectively, to obtain a solution of 20 mg/mL for examination. The injection volume is 25 μL. The flow rate is 1 mL/min. The column temperature is 30° C. A chromatographic analysis diagram of a test sample is shown in FIG. 2-4. It can be seen that the components of the samples cannot be effectively separated under the elution condition.

TABLE 9

Proportions of mobile phase A and mobile phase B in embodiment 10

| Time (min) | Mobile phase A (%) | Mobile phase B (%) |
|---|---|---|
| 0 | 100 | 0 |
| 20 | 100 | 0 |
| 55 | 0 | 100 |
| 70 | 0 | 100 |
| 71 | 100 | 0 |
| 90 | 100 | 0 |

Embodiments 11

A Waters 2695 high performance liquid chromatography and a 2489 multiwavelength ultraviolet detector are used. The wavelength is 275 nm. The chromatographic column has a length of 250 mm and a diameter of 4.6 mm. The packing material for the chromatographic column is tertiary ammonium-bonded polystyrene-divinylbenzene particle with a particle diameter of 5 The mobile phase A is 30 mM 2-(N-morpholino) ethanesulfonic acid containing 3 mM EDTA, the pH of which is adjusted to 5 with a NaOH solution. The mobile phase B is 10 mM 2-(N-morpholino) ethanesulfonic acid containing 2 mM EDTA and 2 M NaCl, the pH of which is adjusted to 6 with a NaOH solution. The proportions of the mobile phase A and mobile phase B are set according to the following Table 10. Mobile phase solutions are added to dissolve the reference substance or the test sample, respectively, to obtain a solution of 20 mg/mL for examination. The injection volume is 25 μL. The flow rate is 1 mL/min. The column temperature is 35° C. The proportions of each component are shown in Table 11.

TABLE 10

Proportions of mobile phase A and mobile phase B in embodiment 11

| Time (min) | Mobile phase A (%) | Mobile phase B (%) |
|---|---|---|
| 0 | 100 | 0 |
| 10 | 100 | 0 |
| 10.1 | 97.5 | 2.5 |
| 15 | 97.5 | 2.5 |
| 15.1 | 93 | 7 |
| 20 | 93 | 7 |
| 20.1 | 90 | 10 |
| 30 | 90 | 10 |
| 30.1 | 87.5 | 12.5 |
| 40 | 87.5 | 12.5 |
| 40.1 | 83 | 17 |
| 50 | 83 | 17 |
| 50.1 | 80 | 20 |
| 60 | 80 | 20 |
| 60.1 | 75 | 25 |
| 75 | 75 | 25 |
| 75.1 | 70 | 30 |
| 85 | 70 | 30 |
| 85.1 | 65 | 35 |
| 95 | 65 | 35 |
| 95.1 | 60 | 40 |
| 105 | 60 | 40 |
| 105.1 | 55 | 45 |
| 115 | 55 | 45 |
| 115.1 | 50 | 50 |
| 125 | 50 | 50 |
| 125.1 | 100 | 0 |
| 140 | 100 | 0 |

TABLE 11

Comparison and analyses of compositions of anion exchanges between three batches of reference substances and three batches of test samples

| Batch number | Component proportions of each elution peak (%) | | | | | | | | | | |
|---|---|---|---|---|---|---|---|---|---|---|---|
| | 1 | 2 | 3 | 4 | 5 | 6 | 7 | 8 | 9 | 10 | 11 |
| Reference Substance 1 | 7.03 | 10.03 | 11.72 | 14.46 | 14.00 | 12.28 | 9.12 | 6.9 | 7.56 | 4.68 | 2.00 |
| Reference Substance 2 | 5.98 | 9.82 | 12.65 | 14.36 | 14.31 | 12.27 | 9.23 | 6.69 | 7.95 | 4.02 | 2.73 |
| Reference Substance 3 | 6.58 | 9.35 | 11.86 | 13.64 | 13.89 | 12.28 | 9.48 | 7.11 | 8.79 | 3.98 | 3.04 |
| Test sample 1 | 5.06 | 7.35 | 10.40 | 12.91 | 13.94 | 12.90 | 10.46 | 8.30 | 11.66 | 4.56 | 2.46 |
| Test sample 2 | 6.02 | 8.60 | 11.83 | 13.42 | 13.98 | 12.47 | 9.69 | 7.28 | 1015 | 3.78 | 3.24 |
| Test sample 3 | 26.28 | 8.62 | 11.60 | 13.76 | 14.18 | 12.37 | 9.48 | 7.05 | 9.66 | 3.96 | 3.06 |

Examples of Reversed-Phase Liquid Chromatography (Embodiments 12-17)

Embodiments 12

An Agilent 1260 high performance liquid chromatography and a multiwavelength ultraviolet detector are used. The wavelength is 275 nm. The chromatographic column has a length of 250 mm and a diameter of 4.6 mm. The packing material for the chromatographic column is C18-bonded silica particle with a particle diameter of 3 The mobile phase A is acetonitrile. The mobile phase B is 50 mM ammonium sulfate, the pH of which is adjusted to 2.5 with a phosphoric acid solution. The proportions of the mobile phase A and mobile phase B are set according to the following Table 12. Mobile phase solutions are added to dissolve the reference substance or the test sample, respectively, to obtain a solution of 20 mg/mL for examination. The injection volume is 25 μL. The flow rate is 1 mL/min. The column temperature is 30° C. The proportions of each component are shown in Table 13, and a chromatographic analysis diagram of a test sample is shown in FIG. 3-1.

TABLE 12

Proportions of mobile phase A and mobile phase B in embodiment 12

| Time (min) | Mobile phase A (%) | Mobile phase B (%) |
|---|---|---|
| 0 | 5 | 95 |
| 5 | 5 | 95 |
| 5.1 | 12.5 | 87.5 |
| 20 | 12.5 | 87.5 |
| 20.1 | 15 | 85 |
| 35 | 15 | 85 |
| 35.1 | 17.5 | 82.5 |
| 50 | 17.5 | 82.5 |
| 50.1 | 20 | 80 |
| 65 | 20 | 80 |
| 65.1 | 22.5 | 78.5 |
| 80 | 22.5 | 78.5 |
| 80.1 | 25 | 75 |
| 95 | 25 | 75 |
| 95.1 | 30 | 70 |
| 110 | 30 | 70 |
| 110.1 | 40 | 60 |
| 125 | 40 | 60 |
| 125.1 | 5 | 95 |
| 135 | 5 | 95 |

TABLE 13

Comparison and analyses of compositions of anion exchanges between three batches of reference substances and three batches of test samples

| Batch number | Component proportions of each elution peak (%) | | | | | | | |
|---|---|---|---|---|---|---|---|---|
| | 1 | 2 | 3 | 4 | 5 | 6 | 7 | 8 |
| Reference Substance 1 | 7.08 | 9.49 | 16.27 | 22.84 | 20.86 | 12.98 | 8.58 | 1.91 |
| Reference Substance 2 | 6.35 | 8.63 | 15.37 | 22.72 | 21.82 | 14.21 | 8.93 | 1.97 |
| Reference Substance 3 | 6.35 | 9.49 | 16.56 | 23.02 | 20.75 | 13.21 | 8.53 | 2.09 |
| Test sample 1 | 4.60 | 7.08 | 14.35 | 22.56 | 23.00 | 15.68 | 10.52 | 2.21 |
| Test sample 2 | 2.42 | 5.15 | 13.41 | 23.71 | 24.41 | 16.80 | 11.48 | 2.62 |
| Test sample 3 | 1.13 | 3.65 | 10.13 | 21.17 | 25.17 | 18.98 | 16.40 | 3.37 |

Embodiments 13

An Agilent 1260 high performance liquid chromatography and a multiwavelength ultraviolet detector are used. The wavelength is 275 nm. The chromatographic column has a length of 250 mm and a diameter of 4.6 mm. The packing material for the chromatographic column is C8-bonded silica particle with a particle diameter of 10 μm. The mobile phase A is acetonitrile. The mobile phase B is 0.1% trifluoroacetic solution. The proportions of the mobile phase A and mobile phase B are set according to the following Table 12. Mobile phase solutions are added to dissolve the reference substance or the test sample, respectively, to obtain a solution of 10 mg/mL for examination. The injection volume is 50 μL. The flow rate is 1 mL/min. The column temperature is 50° C. A chromatographic analysis diagram of a test sample is shown in FIG. 3-2.

Embodiments 14

An Agilent 1260 high performance liquid chromatography and a multiwavelength ultraviolet detector are used. The wavelength is 275 nm. The chromatographic column has a length of 250 mm and a diameter of 4.6 mm. The packing material for the chromatographic column is C4-bonded silica particle with a particle diameter of 10 μm. The mobile phase A is acetonitrile. The mobile phase B is 30 mM ammonium sulfate solution, the pH of which is adjusted to 2 with a phosphoric acid solution. The mobile phase A and mobile phase B are set as Table 12. Mobile phase solutions are added to dissolve the reference substance or the test sample, respectively, to obtain a solution of 20 mg/mL for examination. The injection volume is 15 μL. The flow rate is 0.5 mL/min. The column temperature is 25° C. A chromatographic analysis diagram of a test sample is shown in FIG. 3-3.

Embodiments 15

An Agilent 1260 high performance liquid chromatography and a multiwavelength ultraviolet detector are used. The wavelength is 275 nm. The chromatographic column has a length of 250 mm and a diameter of 4.6 mm. The packing material for the chromatographic column is C4-bonded silica particle with a particle diameter of 3 μm. The mobile phase A is acetonitrile. The mobile phase B is 80 mM ammonium sulfate solution, the pH of which is adjusted to 3 with a phosphoric acid solution. The mobile phase A and mobile phase B are set as Table 12. Mobile phase solutions are added to dissolve the reference substance or the test sample, respectively, to obtain a solution of 20 mg/mL for examination. The injection volume is 25 μL. The flow rate is 0.5 mL/min. The column temperature is 50° C. A chromatographic analysis diagram of a test sample is shown in FIG. 3-4.

Embodiments 16

Figures 1, 2, 3, 4, 5:
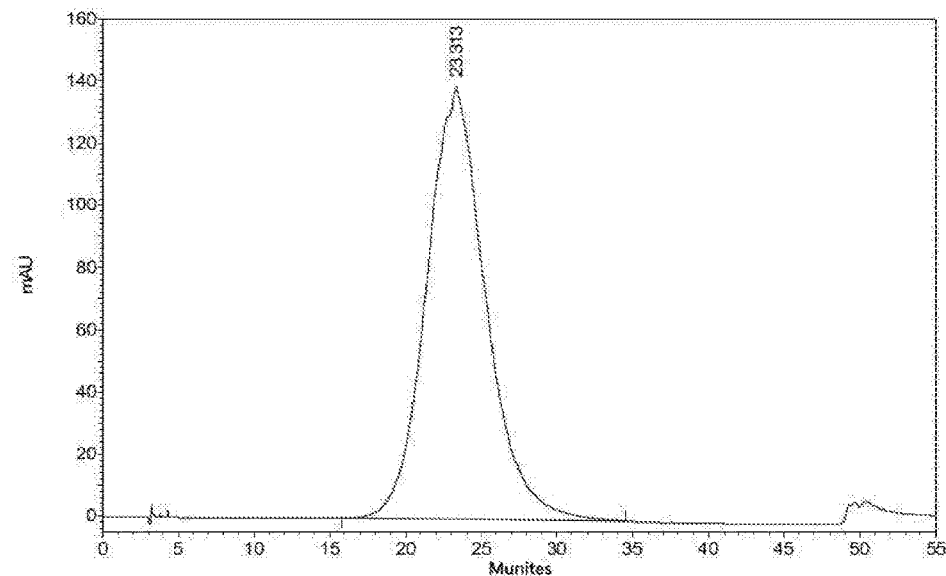
Figures 1, 2:
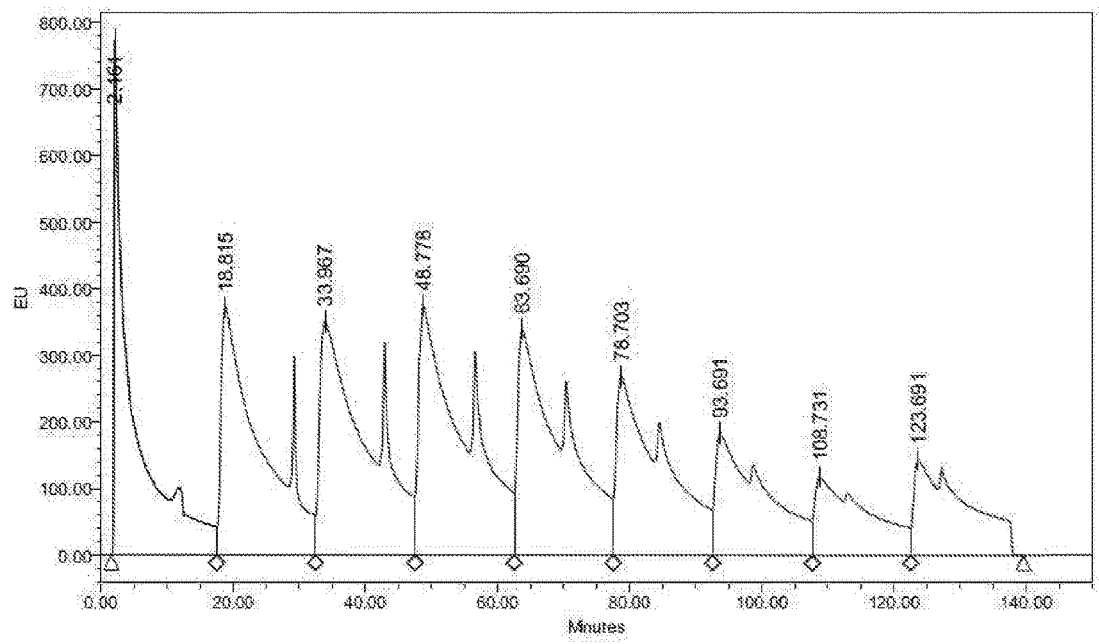
Figure 2:
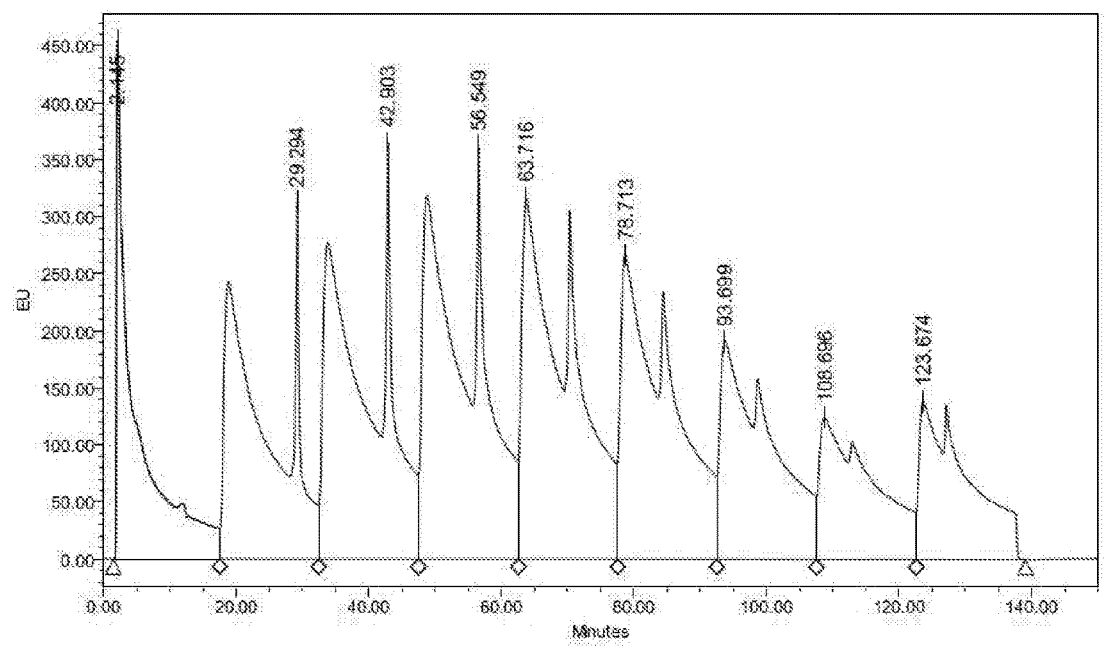
Figures 2, 3:
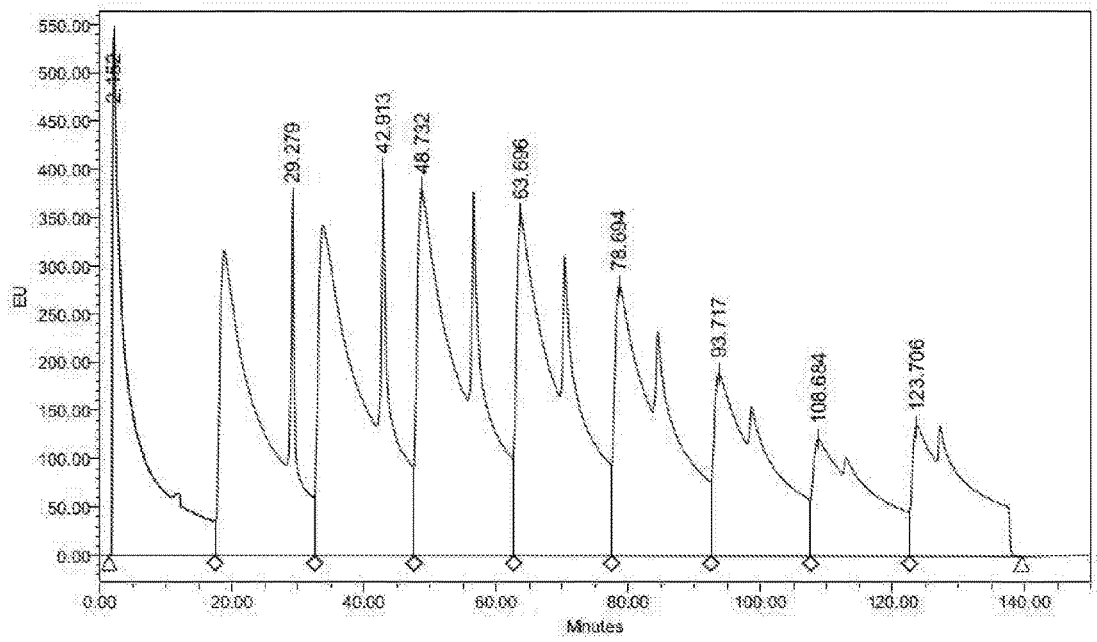
Figures 2, 3, 4:
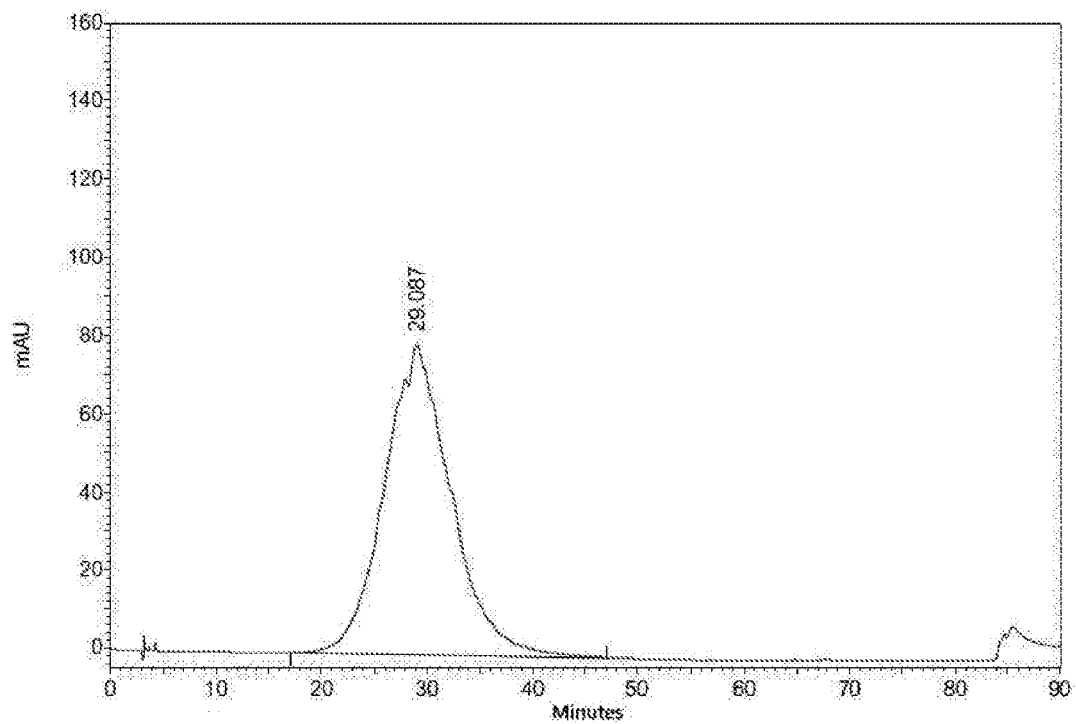
Figures 1, 3:
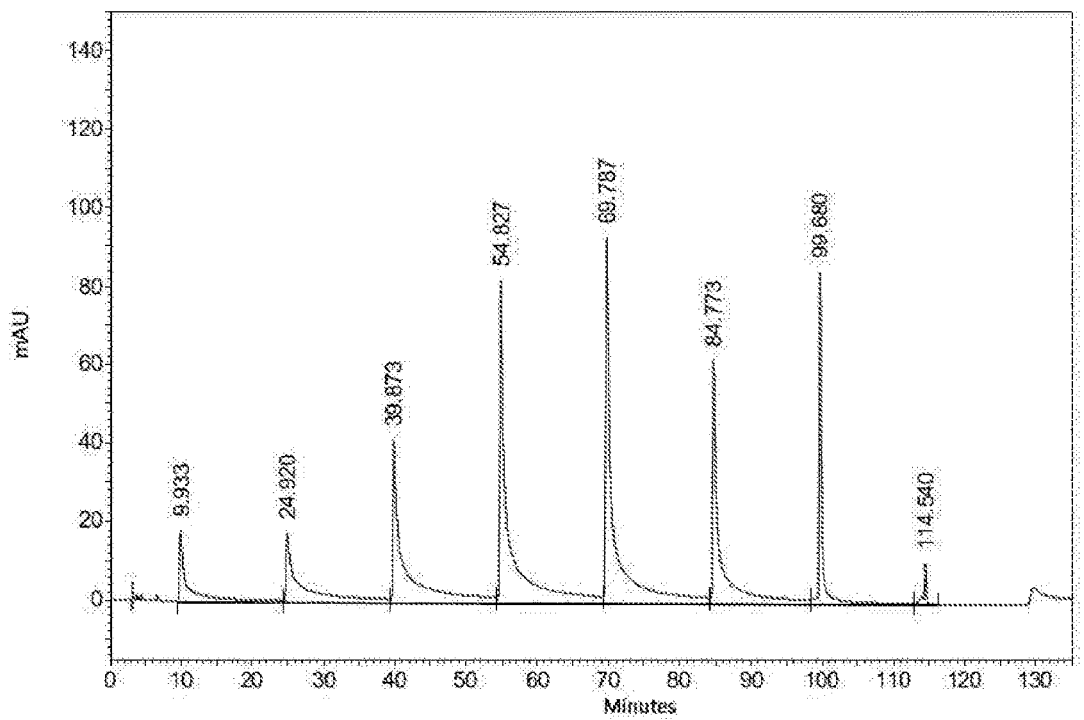
Figures 2, 3:
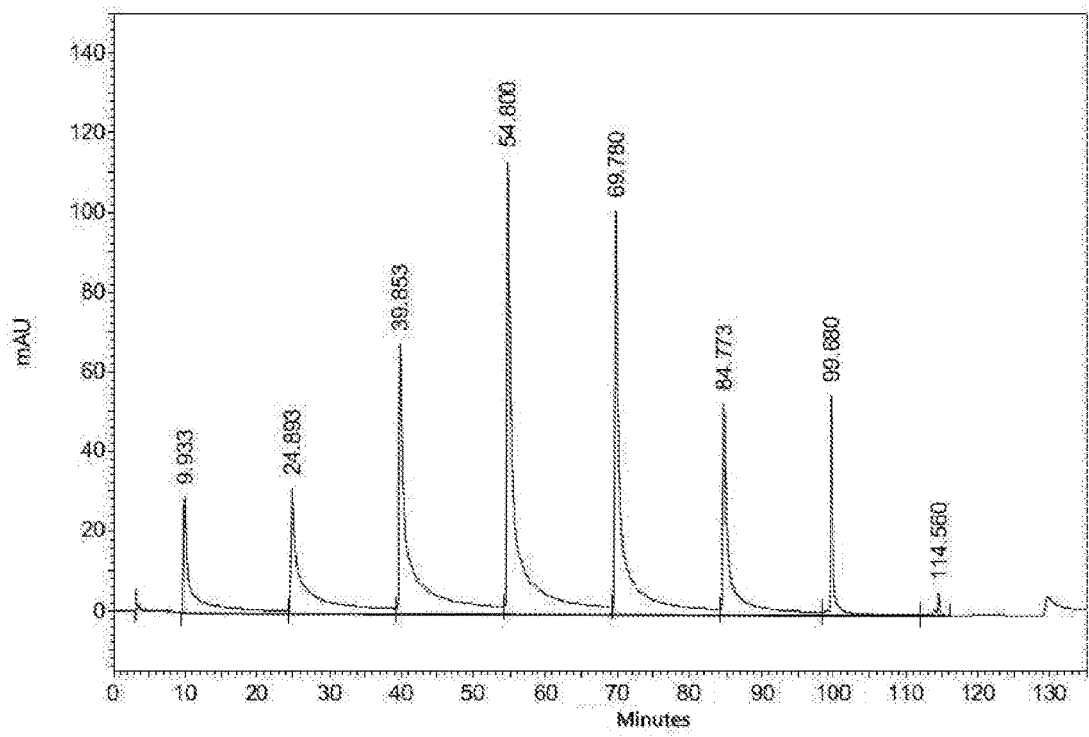
Figure 3:
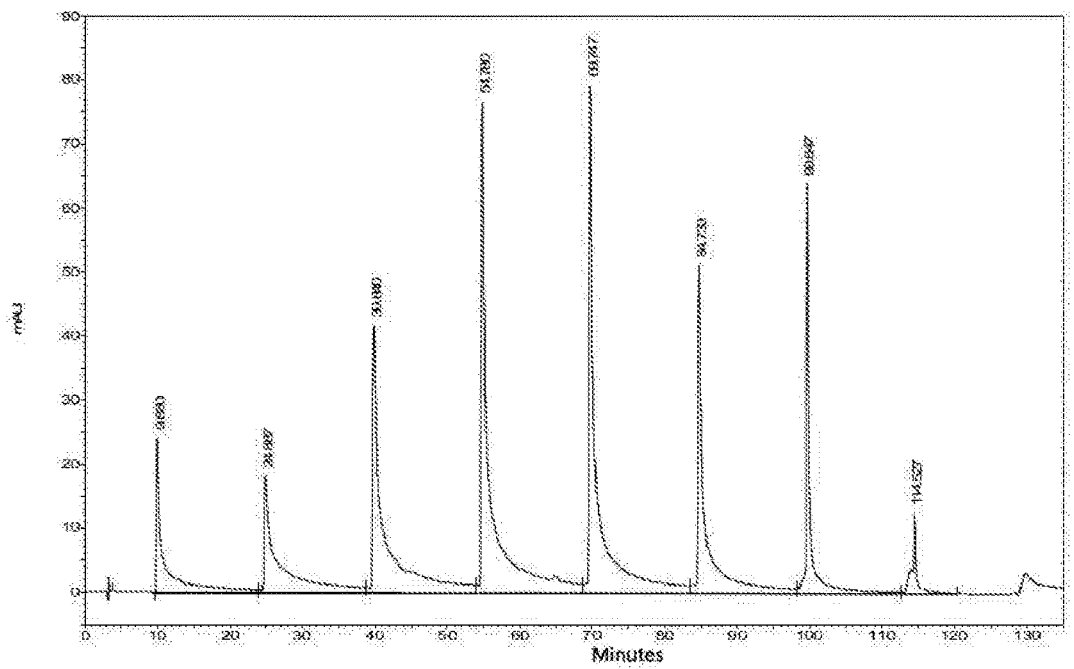
Figures 3, 4:
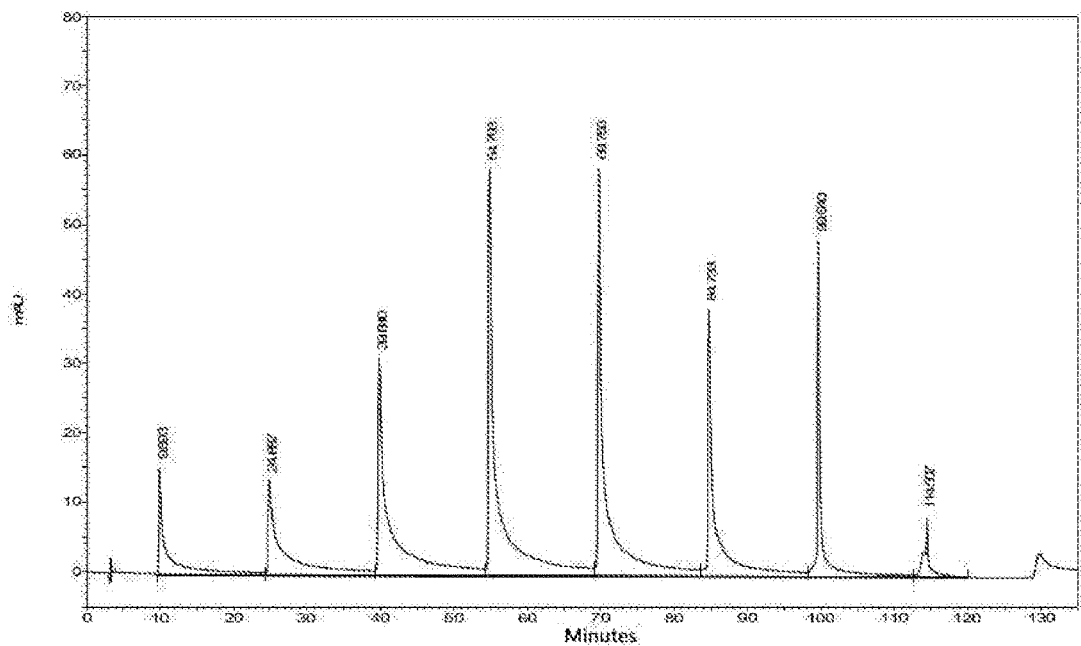
Figures 3, 4, 5:
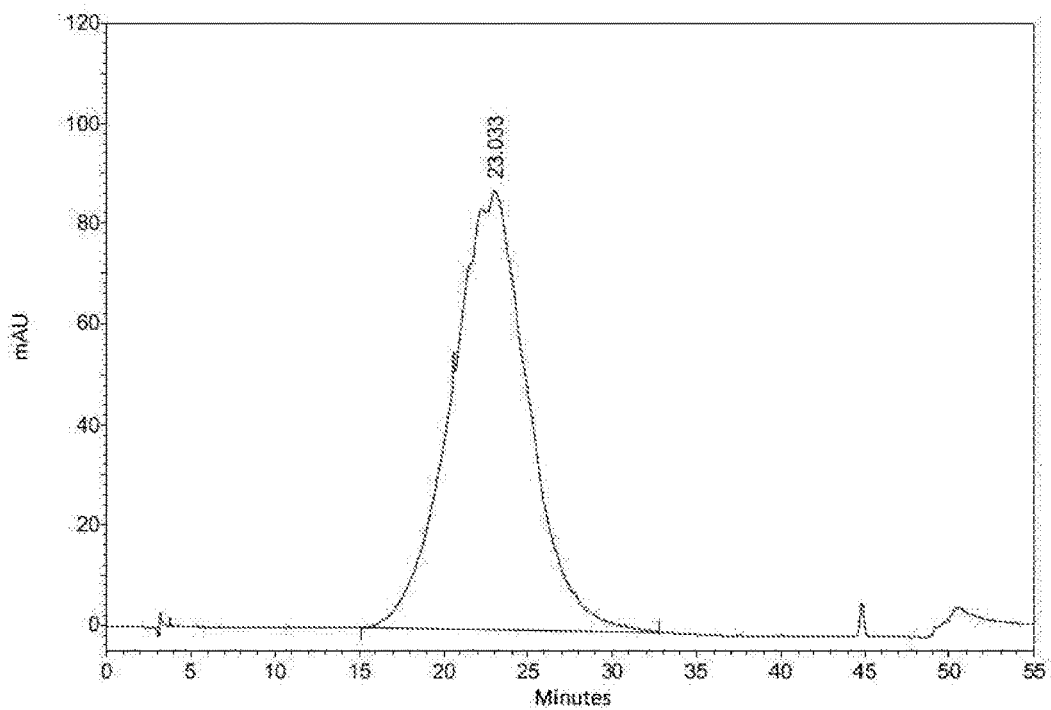

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 250 mm and a diameter of 4.6 mm. The packing material for the chromatographic column is C18-bonded silica particle with a particle diameter of 3 μm. The mobile phase A is acetonitrile. The mobile phase B is 0.1% trifluoroacetic solution. The proportions of the mobile phase A and mobile phase B are set according to the following Table 14. Mobile phase solutions are added to dissolve the reference substance or the test sample, respectively, to obtain a solution of 20 mg/mL for examination. The injection volume is 50 μL. The flow rate is 1 mL/min. The column temperature is 30° C. A chromatographic analysis diagram of a test sample is shown in FIG. 3-5. It can be seen that the components of the samples cannot be effectively separated under the elution condition.

TABLE 14

Proportions of mobile phase A and mobile phase B in embodiment 16

| Time (min) | Mobile phase A (%) | Mobile phase B (%) |
|---|---|---|
| 0 | 100 | 0 |
| 15 | 100 | 0 |
| 35 | 0 | 100 |
| 45 | 0 | 100 |
| 46 | 100 | 0 |
| 55 | 100 | 0 |

Embodiments 17

A Waters 2695 high performance liquid chromatography and a 2475 multiwavelength fluorescence detector are used. The excitation wavelength (Ex) is 230 nm and the emission wavelength (Em) is 300 nm. The chromatographic column has a length of 250 mm and a diameter of 4.6 mm. The packing material for the chromatographic column is C18-bonded silica particle with a particle diameter of 3 μm. The mobile phase A is acetonitrile. The mobile phase B is 0.1% trifluoroacetic solution. The proportions of the mobile phase A and mobile phase B are set according to the following Table 15. Mobile phase solutions are added to dissolve the reference substance or the test sample, respectively, to obtain a solution of 20 mg/mL for examination. The injection volume is 50 μL. The flow rate is 1.5 mL/min. The column temperature is 30° C. The proportions of each component are shown in Table 16.

TABLE 15

Proportions of mobile phase A and mobile phase B in embodiment 17

| Time (min) | Mobile phase A (%) | Mobile phase B (%) |
|---|---|---|
| 0 | 100 | 0 |
| 15 | 100 | 0 |
| 15.1 | 90 | 10 |
| 30 | 90 | 10 |
| 30.1 | 80 | 20 |
| 45 | 80 | 20 |
| 45.1 | 70 | 30 |
| 60 | 70 | 30 |
| 60.1 | 60 | 40 |
| 75 | 60 | 40 |
| 75.1 | 55 | 55 |
| 85 | 55 | 55 |
| 85.1 | 50 | 50 |
| 100 | 50 | 50 |
| 100.1 | 100 | 0 |
| 120 | 100 | 0 |

TABLE 16

Comparison and analyses of compositions of anion exchanges between three batches of reference substances and three batches of test samples

| Batch number | Component proportions of each elution peak (%) | | | | | |
|---|---|---|---|---|---|---|
| | 1 | 2 | 3 | 4 | 5 | 6 |
| Reference Substance 1 | 8.83 | 11.24 | 18.02 | 24.59 | 22.61 | 14.72 |
| Reference Substance 2 | 8.17 | 10.45 | 17.19 | 24.54 | 23.61 | 16.03 |
| Reference Substance 3 | 8.10 | 11.24 | 18.31 | 24.77 | 22.50 | 14.96 |
| Test sample 1 | 6.72 | 9.20 | 16.47 | 24.68 | 25.12 | 17.80 |
| Test sample 2 | 4.77 | 7.50 | 15.76 | 26.06 | 26.76 | 19.15 |
| Test sample 3 | 5.29 | 6.94 | 13.42 | 24.46 | 27.62 | 22.27 |

The embodiments mentioned above indicate that the present invention is effective and feasible in analyzing the content of each component of the glatiramer acetate. Thus, the present invention could be used in the study of comparative analysis and qualification uniformity of the glatiramer acetate product.

It is to be noted that the above embodiments only intend to help the person skilled in the art to understand the spirit of the present invention, but not to limit the scope of the present invention.

We claim:

1. A method for performing linear or stepped gradient elution on a glatiramer acetate with a high-performance liquid chromatography and determining whether the content of each component of the glatiramer acetate is qualified, the method comprising the following steps:
   step (1): preparing a solution of the glatiramer acetate to be tested;
   step (2): performing gradient elution on a sample to be tested with an anion exchange liquid chromatography; and
   step (3): determining a peak area corresponding to each component of the glatiramer acetate, comparing the peak area with a peak area of a reference substance to determine whether the content of each component of the sample to be tested is in a qualified range;
   wherein in step (2), chromatographic conditions for the anion exchange liquid chromatography are as follows:
   carboxyl-bonded polystyrene-divinylbenzene particle with a particle diameter of 1.7-10 μm is used as a packing material for a chromatographic column;
   a first solution containing 10-50 mM tris(hydroxymethyl) aminomethane hydrochloride is used as mobile phase A, wherein pH of the mobile phase A is adjusted to 10-12 with a NaOH solution;
   a second solution containing 10-50 mM tris(hydroxymethyl)aminomethane hydrochloride and 0.5-1.5 M NaCl is used as mobile phase B, wherein pH of the mobile phase B is adjusted to 8-10 with a hydrochloric acid solution;
   an injection volume is 5-50 uL, the concentration of the sample is 1-20 mg/mL;
   a flow rate is 0.5-1.5 mL/min, the time for the gradient elution is 50-250 min;
   gradient of the gradient elution is as follows:
   a total time of the gradient elution is divided into N steps uniformly for gradient elution sequentially, wherein 2≤N≤20,
   in the first N−1 steps, the proportion of the mobile phase A is gradually reduced from 100% to 50%, and the proportion of the mobile phase B is gradually increased from 0 to 50%, in the N-th step, the proportion of the mobile phase A is 100%, and the proportion of the mobile phase B is 0; and a column temperature is 25-50° C.

2. A method for performing linear or stepped gradient elution on a glatiramer acetate with a high-performance liquid chromatography and determining whether the content of each component of the glatiramer acetate is qualified, the method comprising the following steps:

step (1): preparing a solution of the glatiramer acetate to be tested;

step (2): performing gradient elution on a sample to be tested with a cation exchange liquid chromatography; and step (3): determining a peak area corresponding to each component of the glatiramer acetate, comparing the peak area with to a peak area of a reference substance to determine whether the content of each component of the sample to be tested is in a qualified range;

wherein in step (2), chromatographic conditions for the cation exchange liquid chromatography are as follows:

tertiary ammonium-bonded polystyrene-divinylbenzene particle with a particle diameter of 1.7-10 μm is used as a packing material for a chromatographic column;

a first solution containing 10-50 mM 2-(N-morpholino) ethanesulfonic acid and 0.5-5 mM EDTA is used as mobile phase A, wherein pH of the mobile phase A is adjusted to 4-6 with a NaOH solution;

a second solution containing 10-50 mM 2-(N-morpholino) ethanesulfonic acid, 0.5-5 mM EDTA, and 1-2.5 M NaCl is used as mobile phase B, wherein pH of the mobile phase B is adjusted to 5-7 with a hydrochloric acid solution;

an injection volume is 5-50 uL, the concentration of the sample is 1-20 mg/mL;

a flow rate is 0.5-1.5 mL/min, the time for the gradient elution is 50-250 min;

gradient of the gradient elution is as follows:

a total time of the gradient elution is divided into N steps uniformly for gradient elution sequentially, wherein $2 \leq N \leq 20$, in the first N−1 steps, the proportion of the mobile phase A is gradually reduced from 100% to 0%, and the proportion of the mobile phase B is gradually increased from 0 to 100%, in the N-th step, the proportion of the mobile phase A is 90%, and the proportion of the mobile phase B is 10%; and a column temperature is 25-50° C.

3. A method for performing linear or stepped gradient elution on a glatiramer acetate with a high-performance liquid chromatography and determining whether the content of each component of the glatiramer acetate is qualified, the method comprising the following steps:

step (1): preparing a solution of the glatiramer acetate to be tested;

step (2): performing gradient elution on a sample to be tested with a reversed-phase liquid chromatography; and step (3): determining a peak area corresponding to each component of the glatiramer acetate, comparing the peak area with to a peak area of a reference substance to determine whether the content of each component of the sample to be tested is in a qualified range;

wherein in step (2), chromatographic conditions for the reversed-phase liquid chromatography are as follows:

C18-bonded, C12-bonded, C8-bonded, or C4-bonded silica particle with a particle diameter of 1.7-10 μm is used as a packing material for a chromatographic column;

acetonitrile is used as mobile phase A;

a first solution containing 30-80 mM ammonium sulfate is used as mobile phase B, wherein pH of the mobile phase B is adjusted to 2-3 with a phosphoric acid solution;

or 0.1% trifluoroacetic solution is used as the mobile phase B;

an injection volume is 5-50 uL, the concentration of the sample is 1-20 mg/mL;

a flow rate is 0.5-1.5 mL/min, the time for the gradient elution is 50-250 min;

gradient of the gradient elution is as follows:

a total time of the gradient elution is divided into N steps uniformly for gradient elution sequentially, wherein $2 \leq N \leq 20$, in the first N−1 steps, the proportion of the mobile phase A is gradually increased from 5% to 40%, and the proportion of the mobile phase B is gradually reduced from 95% to 60%, in the N-th step, the proportion of the mobile phase A is 90%, and the proportion of the mobile phase B is 10%; and a column temperature is 25-50° C.

4. The method according to claim 1, wherein a detection analysis in step (3) uses an ultraviolet detector to detect a wavelength of 260-280 nm; wherein when a fluorescence detector is used, an excitation wavelength of the fluorescence detector is 230 nm and an emission wavelength of the fluorescence detector is 300 nm.

5. The method according to claim 2, wherein a detection analysis in step (3) uses an ultraviolet detector to detect a wavelength of 260-280 nm; wherein when a fluorescence detector is used, an excitation wavelength of the fluorescence detector is 230 nm and an emission wavelength of the fluorescence detector is 300 nm.

6. The method according to claim 3, wherein a detection analysis in step (3) uses an ultraviolet detector to detect a wavelength of 260-280 nm; wherein when a fluorescence detector is used, an excitation wavelength of the fluorescence detector is 230 nm and an emission wavelength of the fluorescence detector is 300 nm.

7. The method according to claim 1, wherein the total time of the gradient elution is divided into N steps uniformly for gradient elution sequentially, wherein $5 \leq N \leq 15$.

8. The method according to claim 1, wherein the total time of the gradient elution is divided into N steps uniformly for gradient elution sequentially, wherein $8 \leq N \leq 12$.

9. The method according to claim 1, wherein the total time of the gradient elution is divided into N steps uniformly for gradient elution sequentially, wherein N=10.

10. The method according to claim 2, wherein the total time of the gradient elution is divided into N steps uniformly for gradient elution sequentially, wherein $5 \leq N \leq 15$.

11. The method according to claim 2, wherein the total time of the gradient elution is divided into N steps uniformly for gradient elution sequentially, wherein $8 \leq N \leq 12$.

12. The method according to claim 2, wherein the total time of the gradient elution is divided into N steps uniformly for gradient elution sequentially, wherein N=10.

13. The method according to claim 3, wherein the total time of the gradient elution is divided into N steps uniformly for gradient elution sequentially, wherein $5 \leq N \leq 15$.

14. The method according to claim 3, wherein the total time of the gradient elution is divided into N steps uniformly for gradient elution sequentially, wherein $8 \leq N \leq 12$.

15. The method according to claim 3, wherein the total time of the gradient elution is divided into N steps uniformly for gradient elution sequentially, wherein $N=10$.

* * * * *